United States Patent
Wang et al.

(10) Patent No.: US 12,140,586 B1
(45) Date of Patent: Nov. 12, 2024

(54) CALCULATION METHOD FOR SERVICE LIFE OF CONCRETE IN PLATEAU ENVIRONMENT CONSIDERING PROTECTION AND RESTORATION EFFECTS

(71) Applicant: Southeast University, Nanjing (CN)

(72) Inventors: Fengjuan Wang, Nanjing (CN); Yuncheng Wang, Nanjing (CN); Jinyang Jiang, Nanjing (CN); Song Mu, Nanjing (CN); Zhiyong Liu, Nanjing (CN); Yingze Li, Nanjing (CN)

(73) Assignee: Southeast University, Nanjing (CN)

( * ) Notice: Subject to any disclaimer, the term of this patent is extended or adjusted under 35 U.S.C. 154(b) by 0 days.

(21) Appl. No.: 18/444,886

(22) Filed: Feb. 19, 2024

(30) Foreign Application Priority Data

May 25, 2023 (CN) .......................... 202310597741.1

(51) Int. Cl.
*G01N 33/38* (2006.01)
(52) U.S. Cl.
CPC .................................. *G01N 33/383* (2013.01)
(58) Field of Classification Search
CPC .................................................... G01N 33/383
See application file for complete search history.

(56) References Cited

U.S. PATENT DOCUMENTS

| | | | | |
|---|---|---|---|---|
| 7,551,058 B1 * | 6/2009 | Johnson | ............... | G01N 27/226 709/213 |
| 2021/0063336 A1 * | 3/2021 | Ghods | ..................... | G01N 29/07 |
| 2021/0356451 A1 * | 11/2021 | Wang | ..................... | G08B 3/10 |

FOREIGN PATENT DOCUMENTS

| | | | |
|---|---|---|---|
| CN | 111460720 | * | 6/2013 |
| CN | 112694299 | * | 4/2021 |

OTHER PUBLICATIONS

CNIPA, Notification of First Office Action for CN202310597741.1, Nov. 17, 2023.

(Continued)

*Primary Examiner* — Mohamed Charioui
*Assistant Examiner* — Lynda Dinh
(74) *Attorney, Agent, or Firm* — Hemisphere Law, PLLC; Zhigang Ma

(57) ABSTRACT

A calculation method for service life of concrete in a plateau environment considering protection and restoration effects is provided and includes a construction of a model based on a coupling effect of multi-factors of temperature-humidity-salt concentration-load under the plateau environment, simulation of protection and restoration effects, and quantification of service life. The model includes the physical fields of temperature conduction with variable boundary conditions, water dry-wet cycle transport, salt ion transport, and force fields caused by internal and external loads. The simulation of protection and restoration effects include: surface protective coating, damage restoration, and rebar corrosion resistance. The calculation method can simulate the internal temperature, humidity, stress response, and service life of concrete under different plateau environments using the surface protective coating, damage restoration material, and rebar corrosion resistance material, or a combination of protective and damage restoration materials simultaneously.

4 Claims, 10 Drawing Sheets

(56) References Cited

OTHER PUBLICATIONS

Southeast University (Applicant), Reply to Notification of First Office Action for CN202310597741.1, w/ (allowed) replacement claims, Jan. 3, 2024.
CNIPA, Notification to grant patent right for invention in CN202310597741.1, Jan. 3, 2024.

* cited by examiner

CALCULATION METHOD FOR SERVICE LIFE OF CONCRETE IN PLATEAU ENVIRONMENT CONSIDERING PROTECTION AND RESTORATION EFFECTS

CROSS-REFERENCE TO RELATED APPLICATION

This application claims priority to Chinese patent application No. CN 202310597741.1, filed to China National Intellectual Property Administration (CNIPA) on May 25, 2023, which is herein incorporated by reference in its entirety.

TECHNICAL FIELD

The disclosure relates to the technical field of calculation for a service life of concrete, and particularly to a calculation method for service life of concrete in a plateau environment considering protection and restoration effects.

BACKGROUND

China's Sichuan-Tibet Railway, Qinghai-Tibet Expressway and other major national transportation projects are advancing to a plateau area. The plateau area has extreme environmental characteristics such as a maximum temperature difference between day and night of 28° C., relative humidity of 30%-50%, a minimum temperature of −32° C., and a high frequency freeze-thaw with alternating positive and negative temperatures for more than 180 days, ultra-saline soil with a salt concentration exceeding a standard upper limit several times. The coupling effect of large temperature difference, extreme dryness, unsaturated freeze-thaw and saline soil leads to rapid deterioration of concrete performance and difficulty in construction and operation, which causes a severe challenge to the safety service and durability of major traffic projects mainly composed of bridges and tunnels. Surface protection, matrix damage restoration and rebar corrosion restoration are important ways to ensure the durability of reinforced concrete in the plateau environment such as the high frequency freeze-thaw, the large temperature difference and the ultra-saline soil.

At present, domestic and foreign scholars have conducted numerous experiments on concrete corrosion and deterioration under the freeze-thaw, salt corrosion, and dry-wet alternation environments, and the concentration distribution of chloride ions and sulfate ions are collected to predict the service life of the concrete. However, the plateau environment is complex, and protective and restoration materials have numerous types and uneven performance levels. Existing research methods are not accurate in calculating the service life of the concrete in a single plateau environment, and even cannot be applied to calculating the service life of the concrete in a plateau environment with a coupling effect of multi-factors, let alone calculating the service life of the concrete considering protection and restoration effects.

SUMMARY

The disclosure provides a calculation method for a service life of concrete in a plateau environment considering protection and restoration effects to solve the problem that existing methods cannot calculate the service life of the concrete in the plateau environment considering protection and restoration effects.

A calculation method for service life of concrete in a plateau environment considering protection and restoration effects is provided and includes:

determining load parameters composed of a temperature, a humidity, a concentration of salt, and an action situation of internal and external force loads for simulating the plateau environment, and establishing a mapping relationship between the load parameters and time under the plateau environment;

constructing a geometric model of the concrete in the plateau environment considering protection and restoration effects, and determining material properties of phases in the geometric model;

establishing physical field equations under a coupling effect of multi-factors of temperature-humidity-salt concentration-load, and setting, based on the geometric model of the concrete, an internal boundary condition, an external boundary condition and an initial condition of the physical field equations, where the external boundary condition is the mapping relationship between the load parameters and the time under the plateau environment;

solving the physical field equations, and thereby obtaining an internal temperature, an internal humidity, an internal salt concentration, an internal stress distribution of the concrete considering protection and restoration effects under the plateau environment and the load parameters, and changes of the internal temperature, the internal humidity, the internal salt concentration, the internal stress distribution with time; and determining, according to the internal temperature, the internal humidity, the internal salt concentration, the internal stress distribution and the changes of the internal temperature, the internal humidity, the internal salt concentration, the internal stress distribution with time, time corresponding to rebar in the concrete reaching a critical corrosion concentration corresponding to the concrete and the rebar being in a deactivation state, and thereby obtaining the service life of the concrete.

In the mapping relationship between the load parameters and the time under the plateau environment obtained from the calculation method, the temperature, the humidity and the external force load can be constant or changed in any form.

In an embodiment, the constructing a geometric model of the concrete in the plateau environment considering protection and restoration effects includes:

utilizing a Monte Carlo method to randomly generate a microstructure of the concrete; and adding a geometric model of a protective coating with an arbitrary thickness to a surface of the concrete, and thereby obtaining the geometric model of the concrete, wherein the geometric model of the protective coating is a line segment connected with the concrete in a one-dimensional (1D) structural model, the geometric model of the protective coating is a tetrahedron attached to the concrete in a two-dimensional (2D) structural model, and the geometric model of the protective coating is a hexahedron attached to the concrete in a three-dimensional (3D) structural model; and a damage restoration material of the concrete is uniformly distributed in a cement paste of the concrete in a lattice form or a spatial domain form.

The phases in the geometric model of the concrete considering protection and restoration effects include: an aggregate, a slurry and a coating, parameters of the slurry include: an elastic modulus, a Poisson's ratio, a density, a tensile strength, a fracture energy, a phase transition temperature, a phase transition temperature interval, a latent heat of phase change, a thermal conductivity, a constant pressure heat capacity, an ion diffusion coefficient, a porosity and a pore size distribution; parameters of the coating include: a thermal conductivity, a constant pressure heat capacity and an ion diffusion coefficient.

Relevant experimental parameters of the aggregate and the coating are obtained through an experimental testing; the slurry is a composite material composed of a sand and the cement paste; and the parameters of the slurry are obtained through an equivalent medium theory of micromechanics.

In an embodiment, the physical field equations under the coupling effect of the multiple factors include a temperature conduction equation, a water transport equation, a salt transport equation, and a force action equation.

The temperature conduction equation is as follow:

$$\rho C \frac{dT}{dt} = \nabla \cdot (\lambda \nabla T) - L \frac{d\theta}{dt}$$

where $\rho$ represents a density; C represents a specific heat capacity; T represents a temperature; t represents the time; $\lambda$ represents a thermal conductivity; L represents a latent heat of phase change; and $\theta$ represents a water content.

An internal initial temperature of the concrete is set to be consistent with an initial temperature of the plateau environment. And the external boundary condition and the internal boundary condition for the temperature conduction equation are selected as dirichlet boundary conditions, which are consistent with the determined temperature for simulating the plateau environment.

The water transport equation takes into account the two transport effects of gaseous water and liquid water, which are as follows:

$$\frac{\partial \theta}{\partial t} = -\nabla \cdot \left[ \left( \frac{dP_c}{d\theta} \frac{K_{sl} K_{rl}}{\varphi \eta} + \frac{dP_c}{d\theta} \left( \frac{M_w}{RT\rho_l} \right)^2 D_{q0} \varphi^{4/3} (1-\theta)^{10/3} \frac{P_{gs}}{\varphi} e^{\frac{M_w}{RT\rho_l} P_c} \right) \nabla \theta \right]$$

where $P_c$ represents a water characteristic curve; $K_{sl}$ represents a permeability coefficient of water in a material in a saturated state; $\varphi$ represents a porosity; $\eta$ represents a water viscosity; $K_{rl}$ represents a relative permeability coefficient of a liquid phase; $M_w$ represents a molar mass of the water; R represents a relative gas constant; $\rho_l$ represents a density of the water; $D_{g0}$ represents a free diffusion coefficient of water vapor in air; and $P_{gs}$ represents a saturated vapor pressure.

An initial internal moisture content of the concrete is set according to the concrete, ranging from 0 to 100 relative humidity (RH) %. And the external boundary condition and the internal boundary condition for the water transport equation are selected as the dirichlet boundary conditions, which are consistent with the determined water parameters (i.e. the humidity) of the plateau environment.

When salt ion transport only considers convection and diffusion, without considering chemical reactions, the corresponding control equation (i.e. the salt transport equation) is as follows:

$$\frac{\partial c}{\partial t} = \nabla \cdot \left\{ \left[ D_0 \left( \frac{t_0}{t} \right)^m \left( 1 + \left( \frac{1-\theta}{1-\theta_c} \right)^4 \right)^{-1} e^{\frac{U}{R} \left( \frac{1}{T_{ref}} - \frac{1}{T} \right)} \frac{(1-f_r d)}{1+R_b} + f_r d D_f \right] \nabla c - c \frac{dP_c}{d\theta} \frac{K_{sl}}{\varphi \eta} K_{rl} \nabla \theta \right\}$$

where c represents a salt ionic concentration; $D_0$ represents a reference ion diffusion coefficient in a slurry; $t_0$ represents a testing time corresponding to the reference ion diffusion coefficient; m represents a time-dependent coefficient; $\theta_c$ represents a pore critical saturation; U represents an activation energy of an ion in the concrete; $T_{ref}$ represents a testing temperature corresponding the reference ion diffusion coefficient; d represents a damage factor obtained by using a damage mechanics energy method; $f_r$ represents a restoration rate of a restoration material to damage; $D_f$ represents a diffusion coefficient of the ion in the water; and $R_b$ represents an influence factor of the concrete on ion-binding.

The internal initial ion concentration is set to 0, and the external boundary condition and the internal boundary condition for the control equation are selected as the dirichlet boundary conditions, which is consistent with the ion parameters (i.e. the salt concentration) of the plateau environment determined in the calculation method.

The force action equation is as follows:

$$\nabla \cdot \sigma = b \dot{p}*$$

where $\sigma$ represents a stress; b represents a biot's coefficient; and p* represents an equivalent load under the plateau environment, which includes an internal expansion equivalent load caused by freeze-thaw and sulfate.

The internal expansion equivalent load caused by the freeze-thaw in the plateau environment is solved by the following steps:
(i) determining contents of gas, liquid, and ice crystals in the pores of the slurry at a corresponding temperature;
(ii) calculating the internal expansion equivalent load based on the contents of the gas, the liquid, and the ice crystals.

Equations of the step (i) are as follows:

$$r_c = \frac{2\gamma_{CL}}{\sum_m \Delta T} + \delta$$

$$S_{l0}(r) = \begin{cases} 1 - S_G - (\varphi - \varphi(r_{sc})) & r > r_{sc} \\ 1 & r \leq r_{sc} \end{cases}$$

$$S_C(r) = \begin{cases} \begin{cases} S_{l0}(r)/0.917 & S_{l0}(r) < 0.917 \\ 1 & S_{l0}(r) \geq 0.917 \end{cases} & r > r_c \\ 0 & r \leq r_c \end{cases}$$

$$S_L(r) = \begin{cases} 0 & r > r_c \\ S_{l0}(r) & r \leq r_c \end{cases}$$

where $r_c$ represents a critical freezing aperture at the corresponding temperature; $\gamma_{CL}$ represents an ice-water interface energy; $\Sigma_m$ represents an ice-water phase transition entropy; $\Delta T$ represents a temperature difference between the actual temperature in the plateau environment and a freezing point of a solution in the plateau environment under a corresponding pressure, which is affected by the plateau pressure and the pores; $\delta$ represents a thickness of a water film at an edge of a wall of the pore, which is obtained by molecular dynamics simulations of water distribution in unsaturated calcium silicate hydrated (C—S—H gel) pores; $S_{l0}$ (r), $S_C$ (r), $S_L$(r) represents an initial liquid water saturation function, an ice crystal saturation function, and a liquid water saturation function at the corresponding pore size, respectively; $S_G$ represents gas saturation in slurry pores; $r_{sc}$ represents a critical saturated pores, which is also obtained from the molecular dynamics simulations; $\varphi(r_{sc})$ represents a porosity with a pore size smaller than $r_{sc}$.

Equations of the step (ii) are as follows:

$$p_{FT}^* = \frac{1}{\varphi} \int_{r_{min}}^{r_{max}} p_J(r) dr$$

$$p_J(r) = \begin{cases} \dfrac{K\epsilon + b_L \sum_m \Delta T + 3\alpha_s K \Delta T}{b} & C \\ \dfrac{K\epsilon - b_C \sum_m \Delta T + 3\alpha_s K \Delta T}{b} & L \\ P_{atm} - P_{atm0} & G \end{cases}$$

$$\epsilon = -3\left[\alpha_s + \frac{\varphi Mb}{K + b^2 M}(S_C \alpha_C + S_L \alpha_L - \alpha_s)\Delta T\right] +$$

$$\frac{M}{K+b^2M}\left(\frac{b_C}{K_L} - \frac{b_L}{K_C}\right)\sum_m \Delta T + \frac{\varphi Mb}{K+b^2M} S_C\left(1 - \frac{\rho_c^0}{\rho_L^0}\right)$$

where $p_{FT}^*$ represents an internal expansion load force caused by the freeze-thaw; $r_{max}$ and $r_{min}$ represent a maximum pore size and a minimum pore size in a matrix, respectively; $K$, $K_L$ and $K_C$ represent a matrix modulus of the slurry, a matrix modulus of the water and a matrix modulus of ice, respectively; $\epsilon$ represents a strain of the slurry; $b_L$ and $b_C$ represent a biot's coefficient of the water and a biot's coefficient of the ice, respectively; $\alpha_s$ represents a thermal expansion coefficient of the slurry; $P_{atm}$ represents a plateau environmental air pressure; $P_{atm0}$ represents an ambient air pressure when the slurry is poured; $S_C$, $S_L$ and $S_G$ represent a volume fraction of the ice, a volume fraction of the water and a volume fraction of a pore at a corresponding temperature, respectively.

The internal expansion force generated by corrosive ions such as corrosion of the sulfate and undergoing chemical reactions in the pore of the slurry under the plateau environmental can be solved by the following steps: (I) considering the chemical reaction effect, solving the concentration distribution of different ions in the slurry; (II) calculating the volume expansion force of chemical reactions based on the ion concentration distribution.

The corrosion of the sulfate in step (I) is calculated using the following equation:

$$\frac{\partial c_{SO_4^{2-}}}{\partial t} = \nabla \cdot \left(D_{SO_4^{2-}} \nabla c_{SO_4^{2-}} - c_{SO_4^{2-}} \frac{dP_c}{d\theta} \frac{K_{sl}}{\varphi \eta} K_{rl} \nabla \theta\right) - kc_{SO_4^{2-}} c_{CA}$$

$$\frac{\partial c_{Ca^{2+}}}{\partial t} = \nabla \cdot \left(D_{Ca^{2+}} \nabla c_{Ca^{2+}} + D_{Ca^{2+}} c_{Ca^{2+}} \nabla \ln \gamma_{Ca^{2+}}\right)$$

$$\frac{\partial c_{CA}}{\partial t} = -k_2 \frac{c_{gpy} c_{CA}}{q}$$

$$\frac{\partial c_{gpy}}{\partial t} = k_1 c_{SO_4^{2-}} c_{Ca^{2+}} - k_2 c_{gpy} c_{CA}$$

where $c_{SO_4^{2-}}$, $c_{Ca^{2+}}$, $c_{CA}$, and $c_{gpy}$ represent a concentration of sulfate ions, a concentration of calcium ions, a concentration of calcium hydroxide, a concentration of gypsum, respectively; $k$, $k_1$ and $k_2$ represent chemical reaction coefficients; $D_{SO_4^{2-}}$ and $D_{Ca^{2+}}$ represent a diffusion coefficient of the sulfate ions and a diffusion coefficient of the calcium ions, respectively; and q represents a corrosion coefficient of the concrete; and $\gamma_{Ca^{2+}}$ represents an activity of the calcium ions.

The volume expansion force of chemical reactions in step (II) is calculated using the following equations:

$$p_s^* = \frac{RT}{v_{AFt}} \ln\left(\frac{Q_{AFt}}{K_{AFt}}\right)$$

$$\frac{Q_{AFt}}{K_{AFt}} = \frac{(c_{Ca}^p)^6 (c_{Al}^p)^2 (c_{OH}^p)^4 (c_t^p)^3}{(c_{Ca\ eq}^p)^6 (c_{Al\ eq}^p)^2 (c_{OH\ eq}^p)^4 (c_{eq}^p)^3}$$

where $p_s^*$ represents an internal expansion equivalent load caused by corrosion of the sulfate, $v_{AFt}$ represents a volume fraction of an expanded ettringite. $p_s^*$ is determined by combining the concentrations calculated in step (I) with the chemical reaction equation; $c_{Ca}^p$ represents a concentration of calcium ions in a pore solution; $c_{Al}^p$ represents a concentration of aluminum ions in the pore solution; $c_{OH}^p$ represents a concentration of hydroxide ions in the pore solution; $c_t^p$ a concentration of sulfate in the pore solution; $c_{Ca\ eq}^p$ represents an equilibrium concentration the calcium ions in the pore solution; $c_{Al\ eq}^p$ represents an equilibrium concentration the aluminum ions in the pore solution; $c_{OH\ eq}^p$ represents an equilibrium concentration the hydroxide ions in the pore solution; $c_{eq}^p$ represents a saturation concentration of sulfate ions in the pore solution.

The internal expansion force of other corrosive products such as magnesium salts in the slurry can be calculated according to their chemical reaction equation, combined with step (I).

When freeze-thaw occurs and there are corrosive media such as sulfate in the plateau environment, the final internal expansion load on the slurry is calculated as follows:

$$p^* = \sum_{i=1}^{n} \omega_i p_i^*$$

where $\omega_i$ represents a corresponding environmental impact factor; $p_i^*$ represents environmental equivalent loads of the freeze-thaw, the sulfate, and magnesium salt.

According to the numerical model (i.e. the geometric model) of the concrete in the plateau environment considering protection and restoration effects, the physical field equations can be solved using a finite element method.

The service life of the concrete is determined by taking the service life of the rebar at a beginning of reaching the critical corrosion concentration. The ion concentrations at different depths in the concrete through the steps in the calculation method are calculated, the critical corrosion concentration and the ion concentrations are compared to determine the service life of the concrete. A rebar corrosion restoration material increases the critical corrosion concentration of the rebar, and an equation for calculating the service life of the concrete is as follows:

$$t_c = t|_{c(x_d) = f_{rr} * ccr}$$

where $t_c$ represents the service life of the concrete; $x_d$ represents an embedding depth of the rebar; $f_{rr}$ represents an action factor of the rebar corrosion restoration material; ccr represents an inherent critical concentration of corrosion in the rebar.

In an embodiment, the calculation method further includes applying the service life of the concrete in guiding of designing and constructing of another concrete used under the plateau environment.

In an embodiment, the calculation method further includes formulating, by a designer, designs, protection measure, and self-healing measure of concrete for the concrete according to the service life of the concrete.

In an embodiment, the calculation method is implemented by a calculation device including a processor and a memory with a calculation application stored therein. The calculation application, when executed by the processor, is configured to implement the calculation method and is further configured to send, over the Internet, the service life to a mobile terminal of a designer of the concrete. An application installed in the mobile terminal is configured to receive the service life, and display the service life on the mobile terminal to assist the designer to formulate a maintenance measure, and a repair plan for the concrete according to the service life of the concrete.

DETAILED DESCRIPTION OF EMBODIMENTS

Further explanation of the disclosure will be provided below in conjunction with the attached drawings.

A calculation method for service life of concrete in a plateau environment considering protection and restoration effects is provided, and the specific process is as follows.

A concrete pier serving in the plateau environment in China is selected. The concrete pier is in contact with water, with a temperature range of −8-20° C., a chloride concentration of 20000 milligrams per liter (mg/L), sulfate-free, and does not bear additional external loads. Different types of protective coatings of chlorinated polyethylene coating (CPE), chloroprene emulsion coating (CR), polyvinylidene chloride emulsion coating (PVDC) and chlorinated polyvinyl chloride coating (CPVC) are used, and different crack damage restoration materials (with repair rate of 50%, 70% and 90%, respectively) are used, different rebar corrosion restoration materials are used (with critical concentrations increased by 10% and 30%, respectively).

Figure 1:
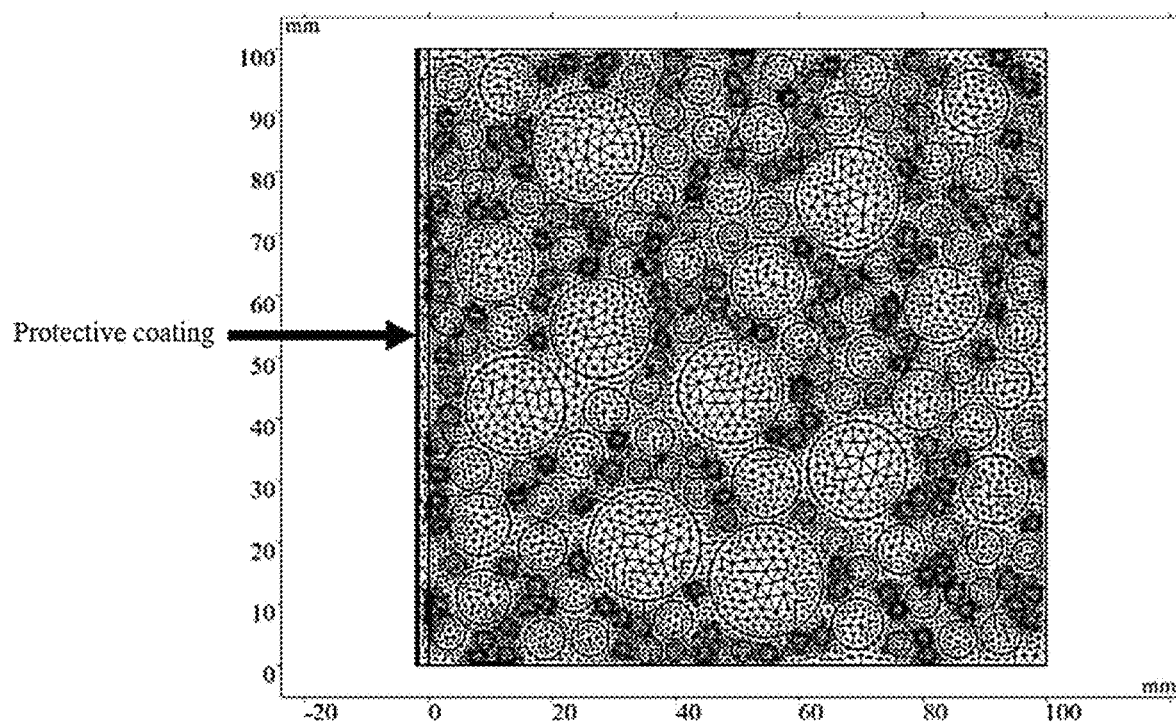
FIG. 1 illustrates a schematic diagram of a two-dimensional (2D) geometric model considering protective and restoration materials.

According to steps of the calculation method, a numerical model in the plateau environment considering protection effects (FIG. 1) is constructed, and followed by solving to obtain the distribution of various parameters in the concrete (i.e. the concrete pier). The chloride ion concentration that is most prone to rebar corrosion is taken as an example (FIGS. 2-8).

Figure 2:
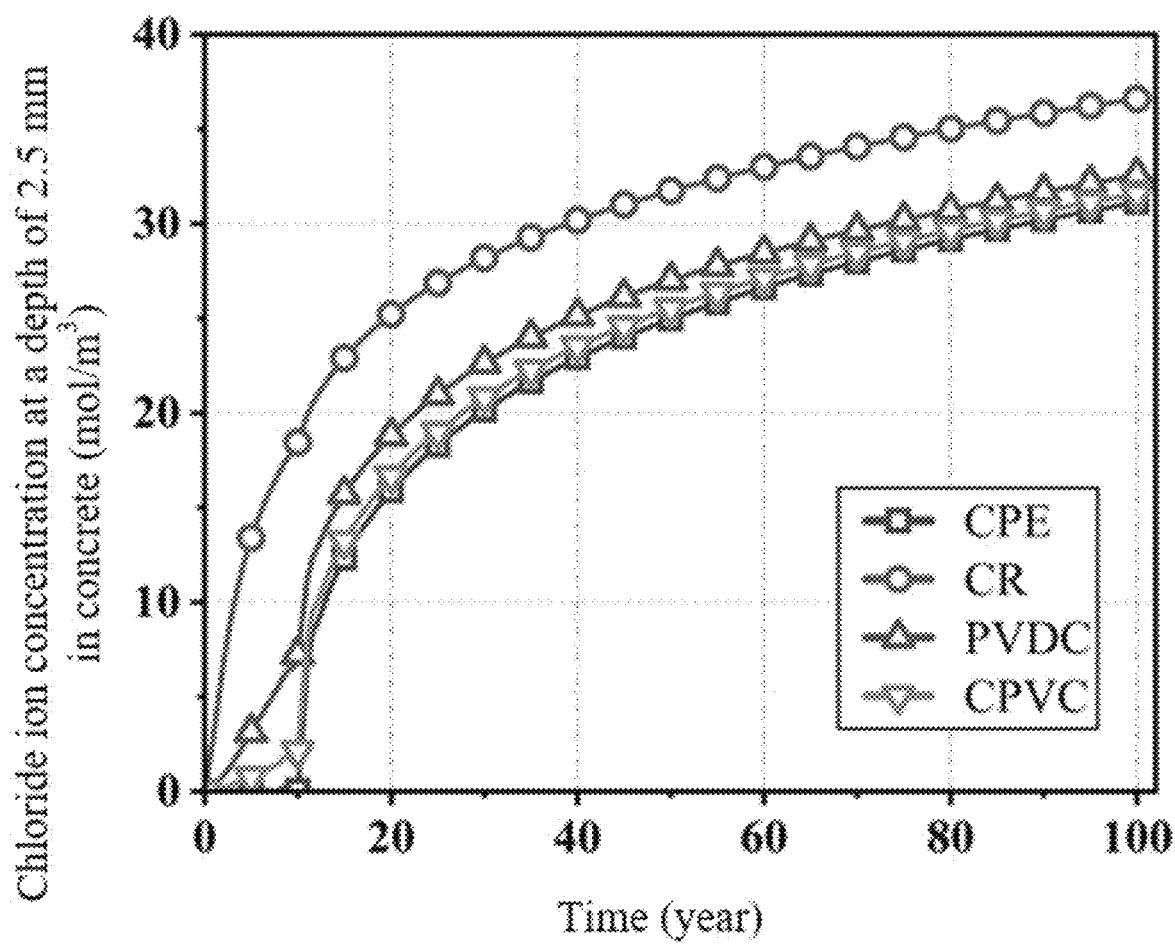
FIG. 2 illustrates a concentration distribution of corrosive media at 0-5 millimeters (mm) on a surface of the concrete after using different types of the protective coatings.

As shown in FIG. 2, it can be seen that within 2 years, neither water nor the chloride ions have passed through the protective coatings. In the $5^{th}$ year, a small amount of water and the chloride ions appeared in the local area on less aggregate of the surface of the concrete. However, within 10 years of the protective coating taking effect, there is no significant amount of water and the chloride ions inside the concrete. This also indicates that the protective coatings have the effects that can effectively isolate water and the chloride ions during the service life of the protective coatings, thereby improving the corrosion resistance of the concrete. After the failure of the protective coating, it means that water and the chloride ions are directly contacted with the surface of the concrete, and then the contents of water and the chloride ions inside the concrete increase significantly. Due to the fact that the chloride ion transport is mainly carried by water and there is adsorption and binding effect inside the concrete, the water transfer rate is much higher than that of the concrete. At the 30th year of the service life, the overall saturation inside the concrete is close to 1, but the chloride ions only exist on the surface of the concrete. The surface protective coating with a service life of 10 years, and at the $15^{th}$ year, the $30^{th}$ year, the $50^{th}$ year, and the $100^{th}$ year, the depth of the chloride ion transport in the concrete is 8 mm, 37 mm, 34 mm, 40 mm, and 48 mm, respectively.

Figure 3:
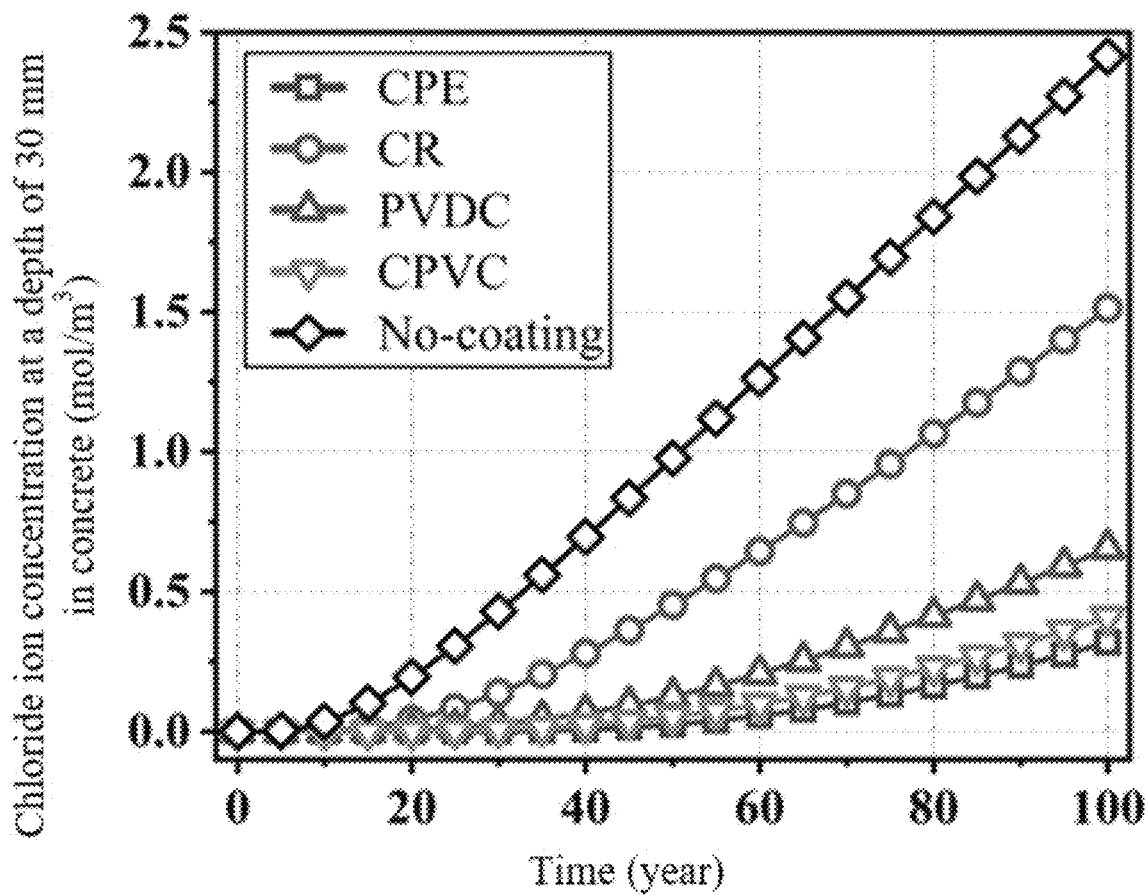
FIG. 3 illustrates a concentration distribution of the corrosive media at a depth of rebar burial after using different types of the protective coatings.

As shown in FIG. 3, the chloride ion concentration in the concrete continues to increase over time, and the growth trend changes from a sharp increase to a slow increase. The use of the protective coatings delays the corrosion time of the chloride ions in the concrete and slows down the diffusion rate of the chloride ions in the concrete. The chloride ion concentration in the concrete is closely related to the service life of the protective coatings. As the service life of the protective coatings increases, the time when the chloride ions begin to corrode the concrete is gradually delayed, and the chloride ion concentration in the concrete also decreases linearly. This indicates that increasing the service life of the protective coatings can effectively reduce the chloride ion concentration in the entire service life of the concrete. An effective means to block and delay chloride ion corrosion and improve the service life of the concrete is to improve the service life of the protective coatings.

Figure 4:
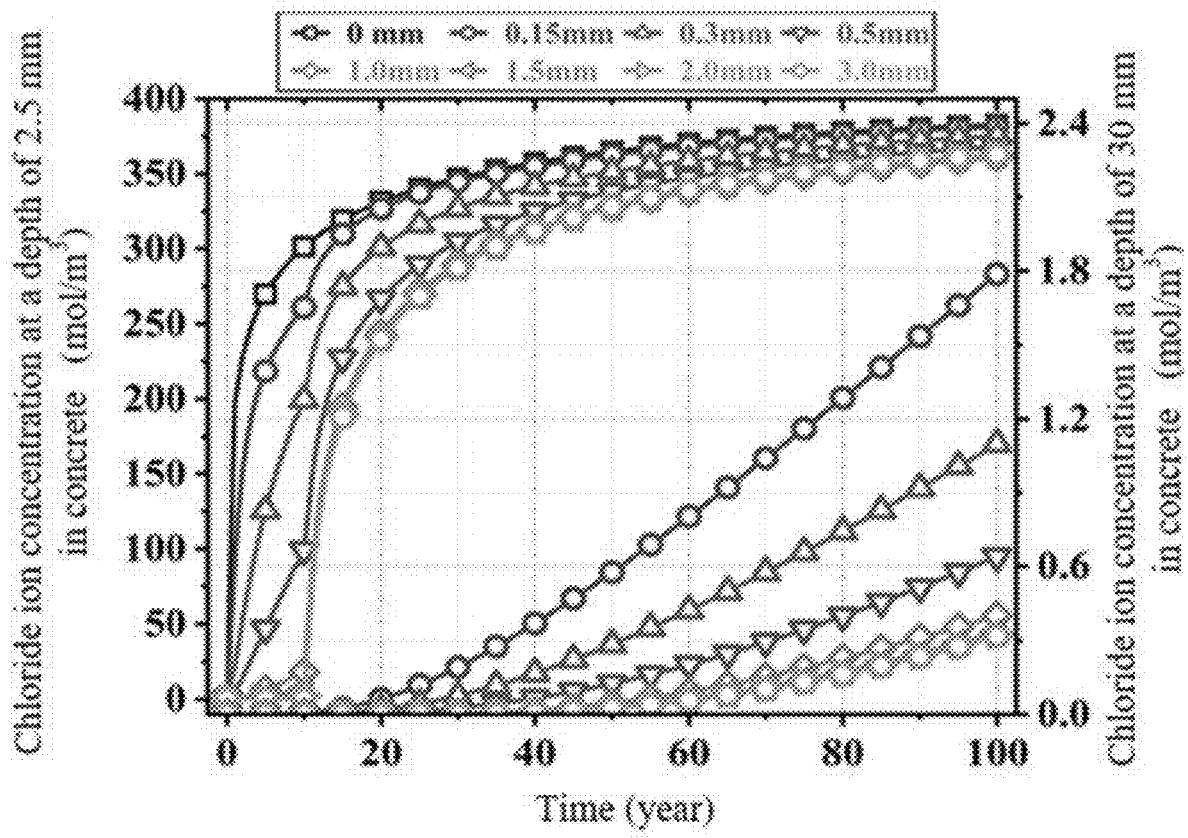
FIG. 4 illustrates a concentration distribution of the corrosive media inside the concrete after using different thicknesses of the protective coatings.

As shown in FIG. 4, increasing the thickness of the protective coatings can effectively reduce the final chloride ion concentration on the surface and inside of the concrete, and the decrease of the chloride ion concentration inside the concrete is more significant than that of on the surface of the concrete. When the thickness of the protective coating is within 1 mm, the time when the chloride ions begin to appear on the surface of the concrete is not delayed. When the thickness of the protective coating exceeds 1 mm, the chloride ion concentration on the surface of the concrete gradually increases. It indicates that the thickness of the protective coating should be at least 1 mm or more in order to effectively block the corrosion of the corrosive media into the concrete within the expected service life of the protective coatings. However, even if the thickness of the protective coating gradually increases to 3 mm, there will still be the chloride ions invading the surface of the concrete.

Figure 5:
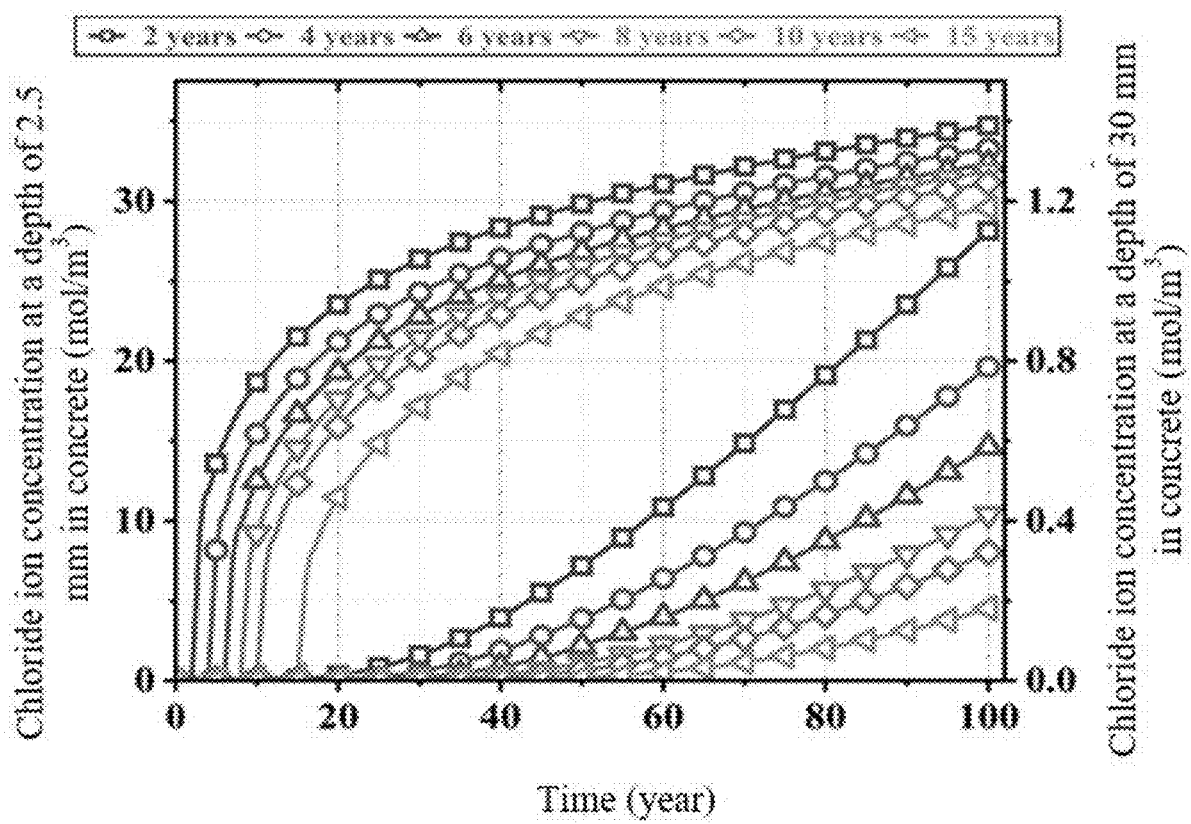
FIG. 5 illustrates a concentration distribution of the corrosive media inside the concrete after using the protective coatings with different service lives.

As shown in FIG. 5, compared with the concrete without using the protective coatings, the final chloride ion concentration of the concrete with four types of the protective coatings, namely the CPE coating, the CR coating, the PVDC coating and the CPVC coating, decreased by 86%, 40%, 70% and 84% respectively. Moreover, the CPE coating, the CR coating, the PVDC coating and the CPVC coating can effectively delay the corrosion time of the chloride ions into the concrete, reduce the chloride ion concentration inside the concrete, and improve the service life of the concrete.

Figure 6:
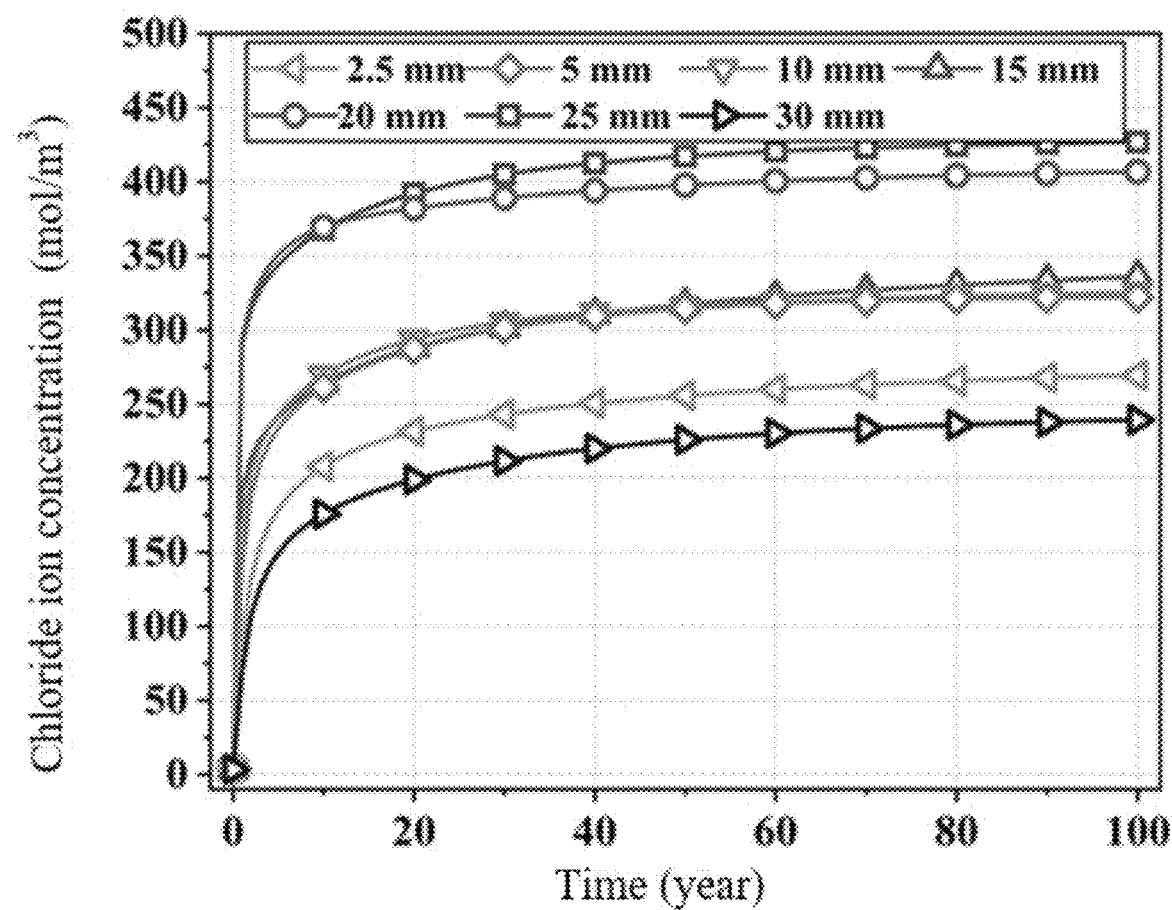
FIG. 6 illustrates a concentration distribution of the corrosive media inside the concrete after using a damage restoration material with a restoration rate of 50%.
Figure 7:
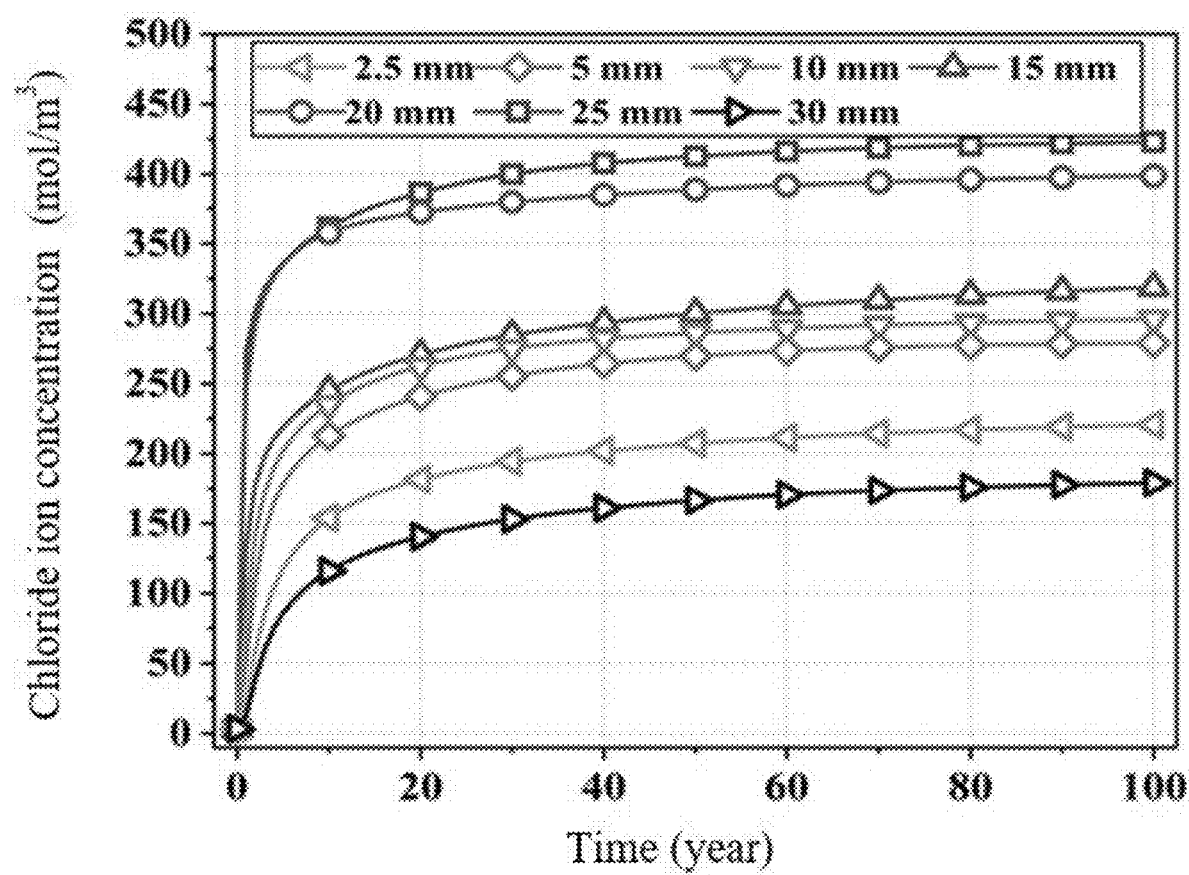
FIG. 7 illustrates a concentration distribution of the corrosive media inside the concrete after using a damage restoration material with a restoration rate of 70%.
Figure 8:
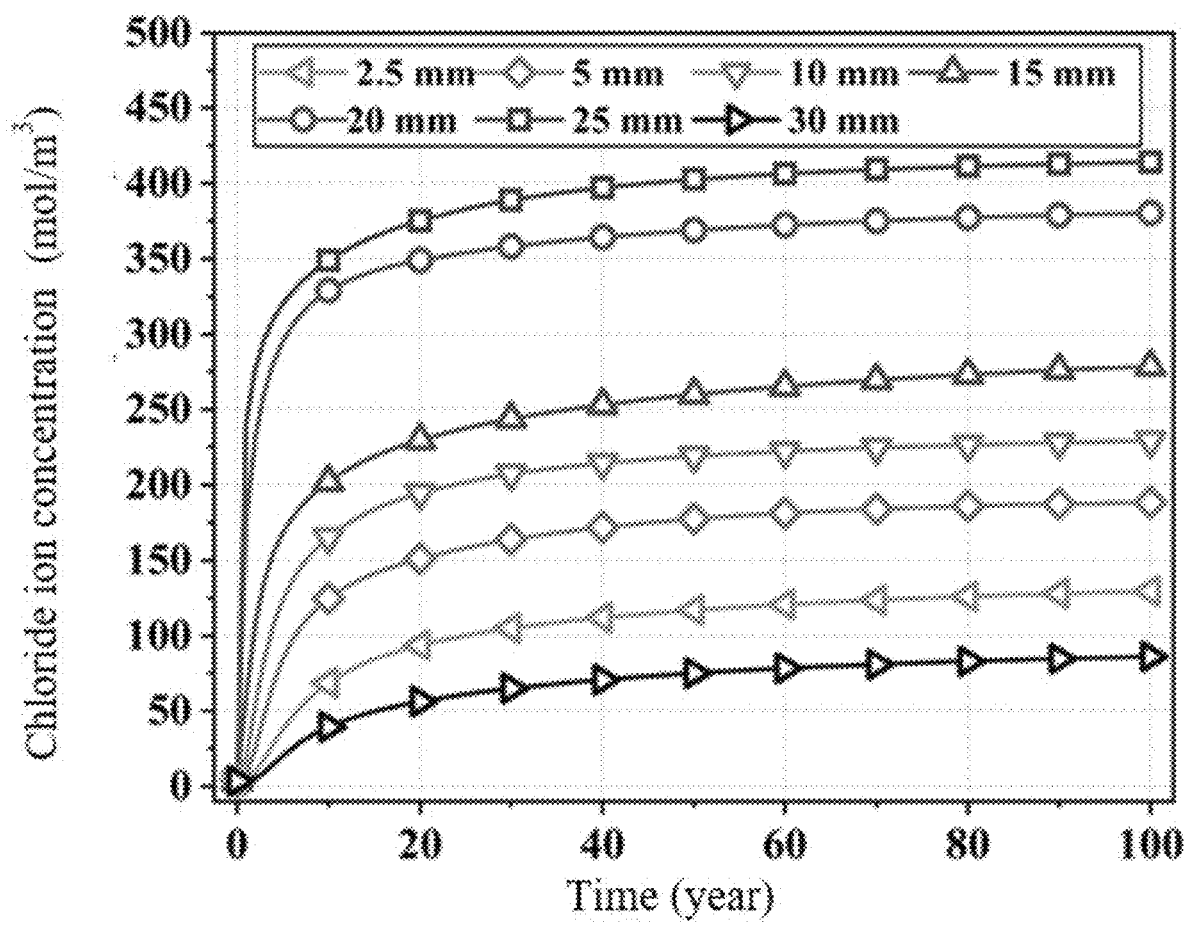
FIG. 8 illustrates a concentration distribution of the corrosive media inside the concrete after using a damage restoration material with a restoration rate of 90%.

As shown in FIGS. 6-8, it can be seen that when the repair rate of the damage restoration material used is 70%, the chloride ion content at a depth of 30 mm in the concrete at 100th year is 73% of that is unrepaired. When the repair rate of the damage restoration material used is 90%, the chloride ion content can be reduced to 35% of which is unrepaired. However, the repair rate of the damage restoration material is in a range of 70%-90%, the damage restoration material has little effect on the transmission of corrosive media within 5 mm depth of the concrete, as the damage has not been completely repaired. Due to the suction effect of the solution in cracks on the surface of the concrete, the corrosive media has already rapidly invaded the interior of the concrete along the cracks. The repair rate of the damage restoration material is in a range of 70%-90%, the damage restoration material has a significant improvement in reducing the concentration of corrosive media within the depth in range of 10-30 mm in the concrete.

Figure 9:
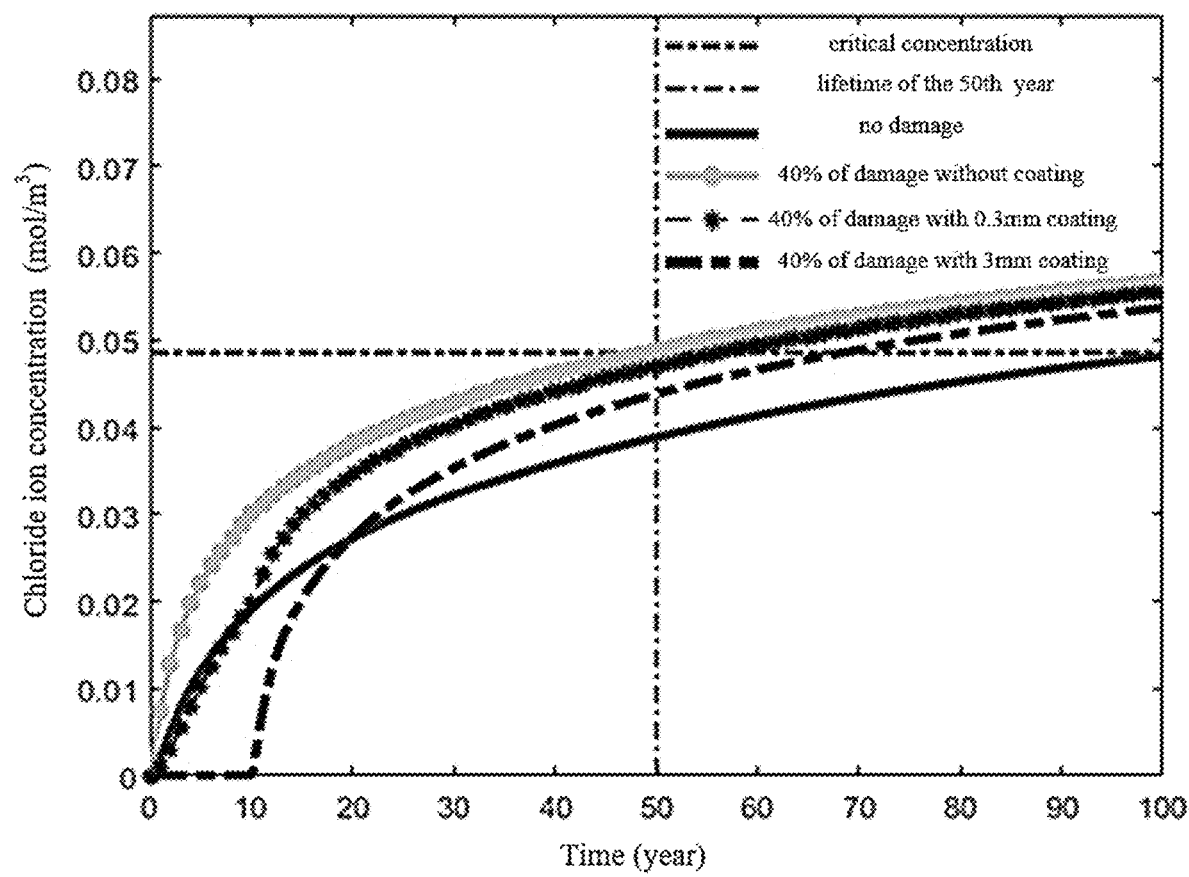
FIG. 9 illustrates a comparison between a concentration of corrosion medium in the concrete and a critical concentration at the depth of the rebar after using of the protective coatings.
Figure 10:
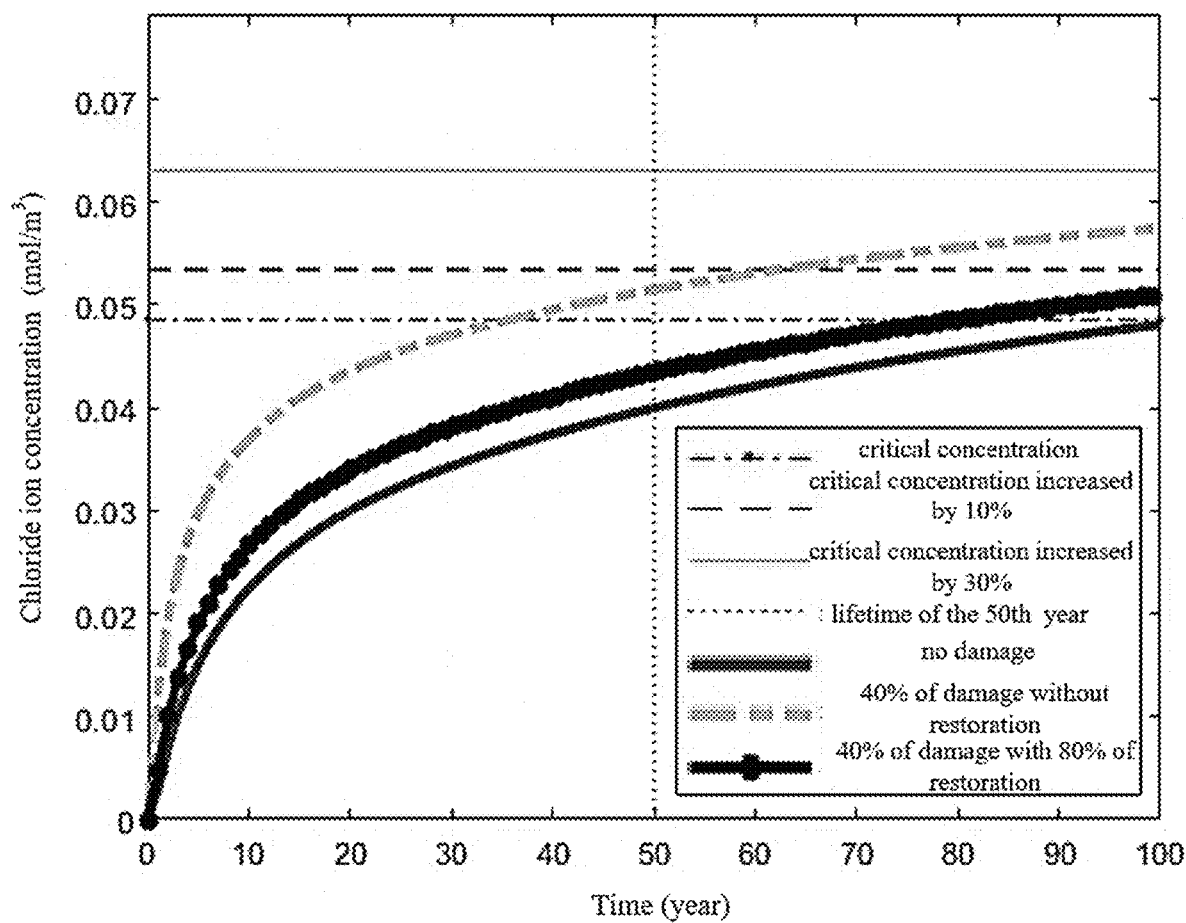
FIG. 10 illustrates a comparison between the concentration of the corrosion medium in the concrete and the critical concentration at the depth of the rebar after using the damage restoration material to repair corroded rebar.

As shown in FIGS. 9-10, the effects of the protective coatings, the damage restoration material, and the rebar corrosion restoration material are considered respectively to calculate the service life of the concrete according to the calculation method.

As shown in FIG. 9, the service life of the concrete damaged by the environment is 50 years. When a 0.3 mm protective coating is used, the service life of the concrete can be increased by only 56 years. When a 3 mm protective coating is used, the service life of the concrete can be increased to 70 years.

As shown in FIG. 10, it can be seen that for the concrete without the use of the protective coatings, and only considering the effects of damage restoration and rebar corrosion restoration, when the concrete only uses a damage restoration material with a damage repair rate of 80%, the concrete can achieve a service life of 78 years. When the concrete only uses the rebar corrosion restoration material that can increase the critical concentration of the concrete by 10%, the service life of the concrete can reach 63 years. When both the damage restoration material and the rebar corrosion restoration material are used simultaneously, the service life of the concrete can be guaranteed to reach 100 years.

Therefore, this method can effectively calculate the service life of the concrete considering protection and restoration effects in the plateau environment, providing important guidance for engineering practice.

What is claimed is:

1. A calculation method for a service life of concrete in a plateau environment for protection and restoration effects, comprising:

S1, determining load parameters composed of a temperature, a humidity, a concentration of salt, and an action situation of internal and external force loads for simulating the plateau environment, and establishing a mapping relationship between the load parameters and time under the plateau environment;

S2, constructing a geometric model of the concrete in the plateau environment for protection and restoration effects, and determining material properties of phases in the geometric model;

S3, establishing physical field equations under a coupling effect of multi-factors of temperature-humidity-salt concentration-load, and setting, based on the geometric model of the concrete, an internal boundary condition, an external boundary condition and an initial condition of the physical field equations, wherein the external boundary condition is the mapping relationship between the load parameters and the time under the plateau environment;

S4, solving the physical field equations, and thereby obtaining an internal temperature, an internal humidity, an internal salt concentration, an internal stress distribution of the concrete for protection and restoration effects under the plateau environment and the load parameters, and changes of the internal temperature, the internal humidity, the internal salt concentration, the internal stress distribution with time; and S5, determining, according to the internal temperature, the internal humidity, the internal salt concentration, the internal stress distribution and the changes of the internal temperature, the internal humidity, the internal salt concentration, the internal stress distribution with time, time corresponding to rebar in the concrete reaching a critical corrosion concentration corresponding to the concrete and the rebar being in a deactivation state, and thereby obtaining the service life of the concrete;

wherein in the S2, the constructing the geometric model of the concrete in the plateau environment for protection and restoration effects comprises:

utilizing a Monte Carlo method to randomly generate a microstructure of the concrete; and adding the geometric model of a protective coating with an arbitrary thickness to a surface of the concrete, and thereby obtaining the geometric model of the concrete, wherein the geometric model of the protective coating is a line segment connected with the concrete in a one-dimensional (1D) structural model, the geometric model of the protective coating is a tetrahedron attached to the concrete in a two-dimensional (2D) structural model, and the geometric model of the protective coating is a hexahedron attached to the concrete in a three-dimensional (3D) structural model; and a damage restoration material of the concrete is uniformly distributed in a cement paste of the concrete in a lattice form or a spatial domain form;

wherein in the S3, the physical field equations under the coupling effect of multiple factors comprise a temperature conduction equation, a water transport equation, a salt transport equation, and a force action equation;

the temperature conduction equation is as follow:

$$\rho C \frac{dT}{dt} = \nabla \cdot (\lambda \nabla T) - L \frac{d\theta}{dt}$$

wherein ρ represents a density; C represents a specific heat capacity; T represents the temperature; t represents the time under the plateau environment; λ represents a thermal conductivity; L represents a latent heat of phase change; and $\theta_L$ represents a water content;

wherein an internal initial temperature of the concrete is set to be consistent with an initial temperature of the plateau environment, and the external boundary condition and the internal boundary condition for the temperature conduction equation are selected as dirichlet boundary conditions, the dirichlet boundary conditions are consistent with the determined temperature for simulating the plateau environment in the S1;

the water transport equation takes into account two transport effects of gaseous water and liquid water, and is expressed as follows:

$$\frac{\partial \theta}{\partial t} = -\nabla \cdot \left[ \left( \frac{dP_c}{d\theta} \frac{K_{sl}K_{rl}}{\varphi \eta} + \frac{dP_c}{d\theta} \left( \frac{M_w}{RT\rho_l} \right)^2 D_{g0} \varphi^{4/3} (1-\theta)^{10/3} \frac{P_{gs}}{\varphi} e^{\frac{M_w}{RT\rho_l}P_c} \right) \nabla \theta \right]$$

wherein $P_c$ represents a water characteristic curve; $K_{sl}$ represents a permeability coefficient of water in a material in a saturated state; φ represents a porosity; η represents a water viscosity; $K_{rl}$ represents a relative permeability coefficient of a liquid phase; $M_w$ represents a molar mass of the water; R represents a relative gas constant; $\rho_l$ represents a density of the water; $D_{g0}$ represents a free diffusion coefficient of water vapor in air; and $P_{gs}$ represents a saturated vapor pressure;

an initial internal moisture content of the concrete is set according to the concrete, ranging from 0 to 100 relative humidity (RH) %, and the external boundary condition and the internal boundary condition for the water transport equation are selected as the dirichlet boundary conditions, the dirichlet boundary conditions are consistent with the determined humidity for simulating the plateau environment in the S1;

when salt ion transport only considers convection and diffusion, without chemical reactions, a corresponding control equation is expressed as follows:

$$\frac{\partial c}{\partial t} = \nabla \cdot \left\{ \left[ D_0 \left( \frac{t_0}{t} \right)^m \left( 1 + \left( \frac{1-\theta}{1-\theta_c} \right)^4 \right)^{-1} e^{\frac{U}{R}\left(\frac{1}{T_{ref}} - \frac{1}{T}\right)} \frac{(1-f_r d)}{1+R_b} + f_r dD_f \right] \nabla c - c \frac{dP_c}{d\theta} \frac{K_{sl}}{\varphi \eta} K_{rl} \nabla \theta \right\}$$

wherein c represents a salt ionic concentration; $D_0$ represents a reference ion diffusion coefficient in the slurry; $t_0$ represents a testing time corresponding to the reference ion diffusion coefficient; m represents a time-dependent coefficient; $\theta_c$ represents a pore critical saturation; U represents an activation energy of an ion in the concrete; $T_{ref}$ represents a testing temperature corresponding the reference ion diffusion coefficient; d represents a damage factor obtained by using a damage mechanics energy method; $f_r$ represents a restoration rate of a restoration material to damage; $D_f$ represents a diffusion coefficient of the ion in the water; and $R_b$ represents an influence factor of the concrete on ion-binding;

wherein an internal initial ion concentration is set to 0, and the external boundary condition and the internal boundary condition for the corresponding control equation are selected as the dirichlet boundary conditions, the dirichlet boundary conditions are consistent with the determined concentration of salt for simulating the plateau environment in the S1;

the force action equation is as follows:

$$\nabla \cdot \sigma = bp^*$$

wherein σ represents a stress; b represents a biot's coefficient; and p* represents an equivalent load under the plateau environment, the equivalent load under the plateau environment includes an internal expansion equivalent load caused by freeze-thaw and sulfate as follows:

$$p^* = \sum_{i=1}^{n} \omega_i p_i^*$$

$$p_{FT}^* = \frac{1}{\varphi} \int_{r_{min}}^{r_{max}} p_J(r) dr$$

$$p_J(r) = \begin{cases} \dfrac{K\epsilon + b_L \sum_m \Delta T + 3\alpha_s K \Delta T}{b} & C \\ \dfrac{K\epsilon - b_c \sum_m \Delta T + 3\alpha_s K \Delta T}{b} & L \\ P_{atm} - P_{atm0} & G \end{cases}$$

$$\epsilon = -3\left[ \alpha_s + \frac{\varphi Mb}{K+b^2M}(S_C \alpha_C + S_L \alpha_L - \alpha_s) \Delta T \right] + \frac{M}{K+b^2M}\left( \frac{b_c}{K_L} - \frac{b_L}{K_C} \right) \sum_m \Delta T + \frac{\varphi Mb}{K+b^2M} S_C \left( 1 - \frac{\rho_c^0}{\rho_L^0} \right)$$

wherein $p_{FT}^*$ represents the internal expansion load caused by the freeze-thaw; $r_{max}$ and $r_{min}$ represent a maximum pore size and a minimum pore size in a matrix, respectively; K, $K_L$ and $K_C$ represent a matrix modulus of the slurry, a matrix modulus of the water and a matrix modulus of ice, respectively; ∈ represents a strain of the slurry; $b_L$ and $b_C$ represent a biot's coefficient of the water and a biot's coefficient of the ice, respectively; $\alpha_s$ represents a thermal expansion coefficient of the slurry; $p_{atm}$ represents a plateau environmental air pressure; $p_{atm0}$ represents an ambient air pressure when the slurry is poured; $S_C$, $S_L$ and $S_G$ represent a volume fraction of the ice, a volume fraction of the water and a volume fraction of a pore at a corresponding temperature, respectively; $p_s^*$ represents the internal expansion equivalent load caused by corrosion of the sulfate, $v_{AFt}$ represents a volume fraction of an expanded ettringite; $\omega_i$ represents a corresponding environmental impact factor; and $p_i^*$ represents environmental equivalent loads of the freeze-thaw, the sulfate, and magnesium salt;

wherein in the S5, the service life of the concrete is determined by taking the service life of the rebar at a beginning of reaching the critical corrosion concentration; ion concentrations at different depths in the concrete through the S1-S4 in the calculation method are calculated, the critical corrosion concentration and the ion concentrations are compared to determine the service life of the concrete; a rebar corrosion restoration material increases the critical corrosion concentration of the rebar, and an equation for calculating the service life of the concrete is as follows:

$$t_C = t|_C(x_d) = f_{rr} * ccr$$

wherein $t_c$ represents the service life of the concrete; $x_d$ represents an embedding depth of the rebar; $f_{rr}$ represents an action factor of the rebar corrosion restoration material; ccr represents an inherent critical concentration of corrosion in the rebar.

2. The calculation method as claimed in claim 1, wherein the mapping relationship between the load parameters and the time under the plateau environment is applicable to the temperature and the humidity in any plateau environment; the salt is multiple corrosive media comprising: sodium chloride (NaCl), calcium chloride (CaCl), cesium chloride (CsCl), sodium sulfate ($Na_2SO_4$) and magnesium sulfate anhydrous ($MgSO_4$); the internal and external force loads comprise: a gravity, an internal pore expansion force and an external load.

3. The calculation method as claimed in claim 1, wherein in the S2, the geometric model of the concrete in the plateau environment for protection and restoration effects comprises a coarse aggregate, a fine aggregate, and the cement paste; grading types of the coarse aggregate and the fine aggregate are randomly set, and a volume fraction of the coarse and fine aggregates in the geometric model is 0%-80%; the protective coating on a surface of the concrete is a continuous coating adhered to the surface of the concrete; the damage restoration material of the concrete is uniformly distributed in the cement paste of the concrete in a field form.

4. The calculation method as claimed in claim 1, wherein in the S2, the phases in the geometric model of the concrete for protection and restoration effects comprise: an aggregate, the slurry and a coating, parameters of the slurry comprise: an elastic modulus, a Poisson's ratio, a density, a tensile strength, a fracture energy, a phase transition temperature, a phase transition temperature interval, the latent heat of phase change, the thermal conductivity, a constant pressure heat capacity, an ion diffusion coefficient, a porosity and a pore size distribution; parameters of the coating comprise: the thermal conductivity, the constant pressure heat capacity and the ion diffusion coefficient; and relevant experimental parameters of the aggregate and the coating are obtained through an experimental testing; the slurry is a composite material composed of a sand and the cement paste; and the parameters of the slurry are obtained through an equivalent medium theory of micromechanics.

\* \* \* \* \*